United States Patent
Sipilä

(10) Patent No.: US 9,070,530 B2
(45) Date of Patent: Jun. 30, 2015

(54) X-RAY TUBE AND X-RAY FLUORESCENCE ANALYSER UTILIZING SELECTIVE EXCITATION RADIATION

(75) Inventor: Heikki Johannes Sipilä, Espoo (FI)

(73) Assignee: OUTOTEC OYJ, Espoo (FI)

(*) Notice: Subject to any disclaimer, the term of this patent is extended or adjusted under 35 U.S.C. 154(b) by 399 days.

(21) Appl. No.: 13/524,522

(22) Filed: Jun. 15, 2012

(65) Prior Publication Data

US 2012/0321038 A1    Dec. 20, 2012

(30) Foreign Application Priority Data

Jun. 15, 2011  (EP) .................................. 11169419

(51) Int. Cl.
| | |
|---|---|
| *H01J 35/10* | (2006.01) |
| *H01J 35/08* | (2006.01) |
| *C23C 14/06* | (2006.01) |
| *C23C 14/34* | (2006.01) |

(52) U.S. Cl.
CPC .................. *H01J 35/08* (2013.01); *C23C 14/34* (2013.01); *H01J 35/10* (2013.01); *H01J 35/108* (2013.01); *C23C 14/06* (2013.01); *H01J 2235/086* (2013.01)

(58) Field of Classification Search
CPC ........... H01J 35/00; H01J 35/02; H01J 35/04; H01J 35/10; H01J 35/108; H01J 2235/08; H01J 2235/081; H01J 2235/083; H01J 2235/084; H01J 2235/088; C23C 10/10; C23C 10/28; C23C 14/00; C23C 14/06; C23C 14/14; C23C 14/34
USPC ........ 378/119, 121, 141–144, 156, 157, 98.8, 378/44–50; 250/370.01, 370.08, 370.09, 250/370.11, 370.14, 505.1, 506.1, 507.1, 250/522.1
See application file for complete search history.

(56) References Cited

U.S. PATENT DOCUMENTS

| | | | | |
|---|---|---|---|---|
| 5,148,462 A * | 9/1992 | Spitsyn et al. | ................ | 378/143 |
| 5,629,969 A * | 5/1997 | Koshishiba | .................. | 378/138 |
| 5,644,612 A * | 7/1997 | Moorman et al. | ........... | 378/98.2 |
| 5,729,584 A * | 3/1998 | Moorman et al. | ............ | 378/146 |
| 5,751,785 A * | 5/1998 | Moorman et al. | ............ | 378/146 |
| 5,835,561 A * | 11/1998 | Moorman et al. | ............. | 378/98 |
| 6,049,589 A * | 4/2000 | Sipila | ............................ | 378/143 |
| 6,649,914 B1 * | 11/2003 | Moorman et al. | ....... | 250/363.06 |
| 6,829,329 B1 * | 12/2004 | Warburton | .................... | 378/143 |
| 2002/0191747 A1 * | 12/2002 | Sato | ............................ | 378/143 |
| 2004/0007671 A1 * | 1/2004 | Sipila et al. | ............. | 250/370.01 |
| 2008/0084966 A1 * | 4/2008 | Aoki et al. | .................... | 378/140 |
| 2010/0098209 A1 * | 4/2010 | Forthmann et al. | .............. | 378/4 |
| 2011/0007872 A1 * | 1/2011 | Steinlage et al. | ............. | 378/62 |
| 2011/0085641 A1 * | 4/2011 | Okunuki et al. | ................ | 378/62 |

FOREIGN PATENT DOCUMENTS

JP    6188092 A    7/1994

OTHER PUBLICATIONS

European Search Report, dated Oct. 12, 2011, from corresponding European application.

* cited by examiner

*Primary Examiner* — Anastasia Midkiff
(74) *Attorney, Agent, or Firm* — Young & Thompson

(57) ABSTRACT

An X-ray tube includes a cathode, an anode with an electron receiving surface, and a window facing the electron receiving surface of the anode. On the electron receiving surface of the anode it includes a layer of anode material. Deeper in the anode than the layer of anode material, there is a block of attenuator material. The atomic number of the attenuator material is less than one third of the atomic number of the anode material.

21 Claims, 3 Drawing Sheets

X-RAY TUBE AND X-RAY FLUORESCENCE ANALYSER UTILIZING SELECTIVE EXCITATION RADIATION

TECHNICAL FIELD

The invention concerns generally the technology of X-ray fluorescence analysers. Especially the invention concerns the task of subjecting the sample to be analysed to excitation radiation of selected energy range.

BACKGROUND OF THE INVENTION

Using X-ray fluorescence analysis to detect and measure the presence of precious metals like gold and/or platinum group metals in a sample requires the excitation radiation to be energetic enough, because said metals have their characteristic X-ray fluorescence peaks relatively far on the energy axis. The same is actually true for all sample constituents that have high enough X-ray fluorescence energies, but precious metals have particular significance because X-ray fluorescence is an important analytical technique to be used for sorting ore in a large industrial scale.

An X-ray tube is traditionally used in an X-ray fluorescence analyser to produce the desired excitation radiation. Electrons emitted from a cathode are accelerated and made to hit an anode. When the accelerated electrons interact with the atoms of the anode, high-intensity X-ray radiation is produced at characteristic energies of the anode material. Additionally there comes the so-called bremsstrahlung, which is X-ray radiation at a continuous distribution of energies. The highest-energy bremsstrahlung comesat energies higher than the characteristic peaks, with the bremsstrahlung cut-off energy corresponding to the voltage used to accelerate the electrons (for example an X-ray tube using a 60 kV acceleration voltage can produce bremsstrahlung photons not more energetic than 60 keV). In order to analyse heavy elements like the precious metals mentioned above through X-ray fluorescence, the most energetic part of the bremstrahlung is typically needed for excitation. Few or no anode materials are known that would have high enough characteristic energies that could be used as excitation radiation and that would avoid overlapping with the characteristic energies of the elements to be measured.

In an X-ray fluorescence analysis where highly energetic excitation radiation is needed, the lower end of the bremsstrahlung (and, actually, even the characteristic peaks of the anode material) is only a nuisance. Photons of the excitation radiation get scattered by the sample material, and a quite significant number of them find their way into the detector, causing continuous-spectrum background noise. Especially the signal processing electronics coupled to an energy dispersive detector are unnecessarily loaded by scattered excitation radiation that does not carry any meaningful information of the sample material.

A prior art XRF analyser is schematically illustrated in FIG. 1. The illustrated analyser configuration uses an X-ray tube of the so-called side window type. Electrons become detached from a cathode 101 and are accelerated towards an anode 102 with a high voltage coupled between the electrodes. As a result, a beam of X-rays 103 is generated that exits the X-ray tube through a window 104 on its side. A heating unit 105 is needed to heat up the cathode 101, and a cooling unit 106 transfers away the heat generated in the anode 102 by that part of the accelerated electrons' energy that did not exit the X-ray tube in the form of X-rays. A filter 107, conventionally referred to as the primary filter, is placed on the path of the beam of X-rays 103, in order to shape its energy spectrum. The filtered beam of excitation radiation 108 hits the sample 109, the element composition of which is to be analysed. As a result, fluorescent radiation 110 is produced. A detector 111 receives some of the fluorescent radiation 110 and produces a measurement signal, which is processed further in processing electronics 112.

Assuming that the analyser is built for analysing heavy elements in the sample 109, the main purpose of the primary filter 107 is to absorb that part of the generated beam of X-rays 103 that is too soft to be used as excitation radiation, or more specifically those of the generated X-rays that would overlap with the characteristic peaks of the sample material(s) to be analysed. FIG. 2 illustrates a schematic comparison of the originally generated beam of X-rays 103 and the filtered beam of excitation radiation 108. Most importantly the long "tail" that in the upper diagram represents the soft end of the bremsstrahlung is missing in the lower diagram. However, also the overall intensity of the highest-energy X-rays is decreased. This comparison underlines an important drawback of prior art solutions: simply filtering out the softer X-rays will inevitably also affect the intensity of the harder, desired X-rays. In order to produce a high enough intensity of excitation radiation in the arrangement of FIG. 1, the X-ray tube must be operated at a very high power, which means e.g. using relatively large amounts of energy in both the heating unit 105 and the cooling unit 106.

SUMMARY OF THE INVENTION

According to an advantageous embodiment of the invention, an X-ray tube and an X-ray fluorescence analyser are presented where a beam of highly energetic excitation radiation can be produced with good efficiency. According to another advantageous embodiment of the invention, an X-ray tube and an X-ray fluorescence analyser are presented where the contribution of scattered excitation radiation to the detected and analysed radiation can be lowered. According to yet another advantageous embodiment of the invention, an X-ray tube and an X-ray fluorescence analyser are presented that are applicable to accurate industrial X-ray fluorescence analysis of precious metals in for example mining and ore processing industry.

Objectives of the present invention are achieved by using structural solutions that decrease the amount of softer bremsstrahlung that reach the sample to be analysed. These include the use of a thin layer of heavy anode material on top of a block of lighter attenuator material, and a primary filter configured to attenuate the softer end of the excitation radiation up to the characteristic peaks of the anode material. It is advantageous to arrange the propagation directions of the accelerated electrons, the excitation beam, and the fluorescence beam at essentially right angles at each other to take advantage of polarisation effects. A secondary X-ray filter of low-pass type between the sample to be analysed and the detector further reduces the undesired reception of scattered excitation radiation at the detector. Yet another structural solution is to use a germanium-based solid-state detector, in which the germanium detector layer is thin enough in the propagation direction of fluorescent X-rays to let most of the scattered excitation radiation to pass through it.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

The exemplary embodiments of the invention presented in this patent application are not to be interpreted to pose limitations to the applicability of the appended claims. The verb "to comprise" is used in this patent application as an open limitation that does not exclude the existence of also unrecited features. The features recited in depending claims are mutually freely combinable unless otherwise explicitly stated.

DETAILED DESCRIPTION OF THE INVENTION AND ITS EMBODIMENTS

Figure 1:
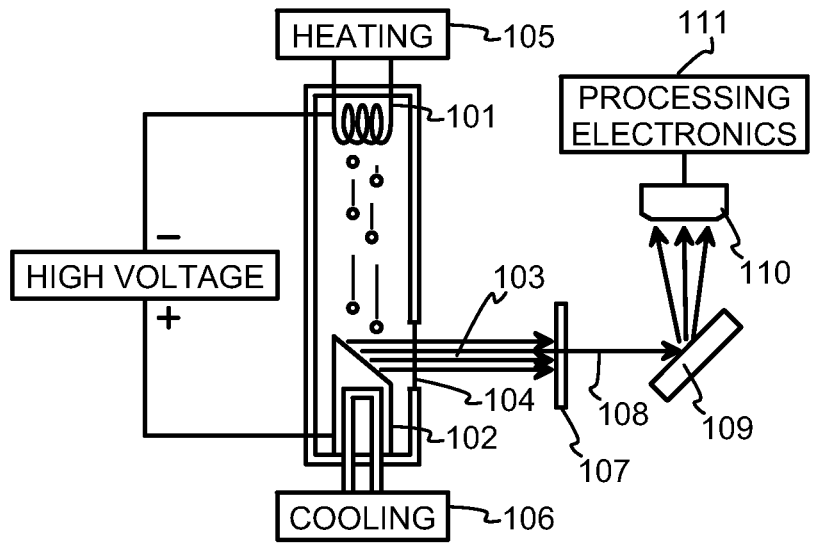
FIG. 1 illustrates a prior art X-ray fluorescence analyser device.
Figure 2:
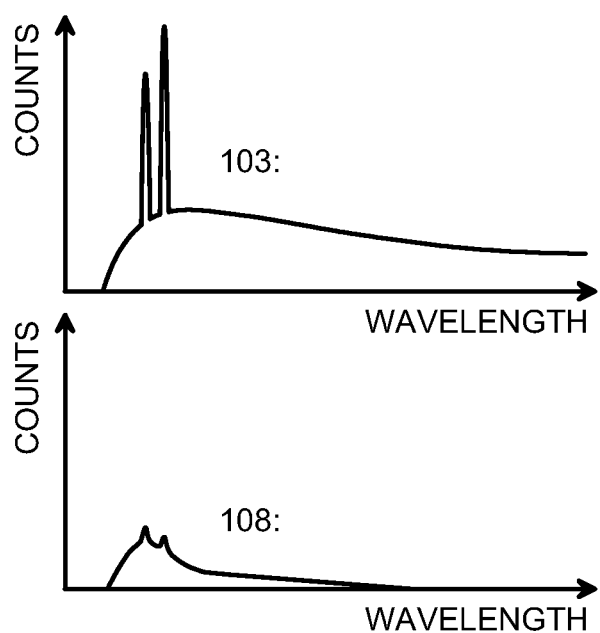
FIG. 2 illustrates spectra of excitation X-rays before and after the primary filter in the apparatus of FIG. 1, FIG. 3 compares the emission of photons of bremsstrahlung in two cases.
Figure 3:
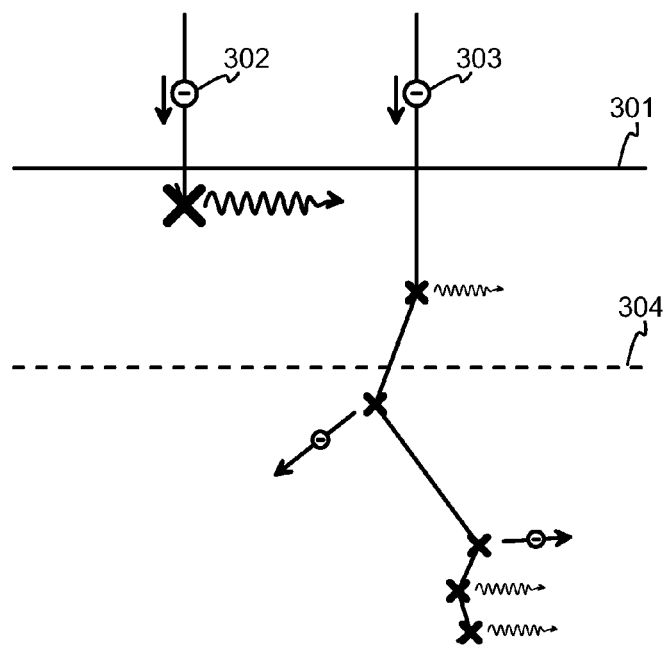

FIG. 3 illustrates a comparison between two electrons that have been accelerated with the same acceleration voltage and that hit the same anode, the electron receiving surface of which is illustrated as 301. The electron 302 on the left in FIG. 3 loses its whole kinetic energy in a single event of interacting with an atom or nucleus of the anode material. As a result, a single photon of bremsstrahlung is emitted, the energy of the emitted photon being essentially equal to the kinetic energy that the electron 302 had at the moment of hitting the anode. This is the high energy limit of the emitted photon. In comparison, the electron 303 on the right in FIG. 3 interacts several times with atoms of the anode material, each time emitting a photon of bremsstrahlung or ejecting an electron from an atom. However, since only the sum of the energies of these photons and electrons equals the initial kinetic energy of the electron 303, each individual photon has necessarily a significantly lower energy. These photons become constituents of the "tail" of softer X-rays that is clearly visible e.g. in the upper spectrum of FIG. 2.

Knowing that the anode material has a certain spatial density of electrons, and that each electron has a certain interaction cross-section with incoming accelerated electrons, it may be shown that the probability of an incoming accelerated electron reaching a certain depth 304 in the anode material without interacting even once with an atom or nucleus of the anode material is very small (the smaller the deeper in the anode material the depth 304 is drawn). This same fact can be stated in different words so that a significant majority (the relative magnitude of which is determined by the definition of the depth 304) of the most energetic bremsstrahlung comes from parts of the anode that are not deeper than the depth 304 from the electron-receiving surface 301. Simplifying only a little, we may say that all useful hard bremsstrahlung comes from the layer of anode material between the electron-receiving surface 301 and the depth 304.

As a thought experiment we might consider, what would happen if the anode actually consisted of a thin foil, i.e. only of the layer between the electron-receiving surface 301 and the depth 304. As a first consequence there would be a number of (still quite energetic) electrons emerging from behind the anode (in FIG. 3, downwards from the fictitious surface at depth 304). Free-flying energetic electrons constitute beta radiation, which as such is ionizing and capable of creating bremsstrahlung in a poorly controlled manner. Additionally even a significant amount of the bremsstrahlung generated within the anode foil would escape from behind the anode. Thus if only a thin foil was used as an anode, care should be taken to keep the energetic electrons and radiation photons emitted at its back side from causing unwanted effects.

As a second consequence, keeping the anode cool enough could pose a problem. Only around one percent of the kinetic energy of the incoming electrons can be eventually utilized in the form of X-rays. The rest is converted into heat, which had to be transported away from the anode foil. Very thin, even foil-like anodes are indeed used in some X-ray tubes of the end window type, but especially the required heat management typically limits their possible operating power to relatively modest levels. If such a foil anode is made thick enough to ensure that no energetic electrons will come through, no selectivity is achieved in the energy range of the created X-rays, because also all interactions of the type shown on the right in FIG. 3 will take place.

The generation of bremsstrahlung depends on the atomic number of the material that is bombarded with the accelerated electrons. An approximate form of this dependency can be expressed with the formula $$N(E) = \frac{KZ(E_0 - E)}{E} \tag{1}$$

Where N(E) is the number of bremsstrahlung photons of energy E created in a time unit, K is the so-called Kramers' constant, Z is the atomic number of the material that is bombarded with the accelerated electrons, and $E_0$ is the initial kinetic energy of the electrons at the time when they hit the anode. We may define a parameter $\Delta E$ so that for use as excitation radiation in an X-ray fluorescence analyser that is capable of accelerating electrons to the maximum energy $E_0$, only the hardest bremsstrahlung with its energy E in the range $$E_0 - \Delta E < E \leq E_0 \tag{2}$$

is desired. If the anode is made of a solid block of a material that has an atomic number $Z_1$, the number $N_1$ of bremsstrahlung photons at the highest undesired energy $E_0 - \Delta E$ is $$N_1(E_0 - \Delta E) = \frac{KZ_1 \Delta E}{\Delta E} = KZ_1 \tag{3}$$

However, if the anode was made of a solid block of a material that has an atomic number $Z_2$ that is, say, one third of the atomic number $Z_1$, the number $N_2$ of bremsstrahlung photons at the highest undesired energy $E_0 - \Delta E$ would be $$N_2(E_0 - \Delta E) = \frac{KZ_2 \Delta E}{\Delta E} = KZ_2 = K\frac{Z_1}{3} = \frac{N_1}{3}, \tag{4}$$

in other words only one third of the number $N_1$ of bremsstrahlung photons with the heavier anode material. The same expression is true for all undesired bremsstrahlung photons energies smaller than $E_0 - \Delta E$.

The observation that the intensity at which an anode material produces bremsstrahlung photons is proportional to its atomic number can be combined with the previous observation, according to which all useful hard bremsstrahlung comes from the layer of anode material between the electron receiving surface and a certain relatively small depth. As a result, if an anode is made to comprise at least two different materials, with a heavier material layer covering a lighter material on the electron receiving surface, a significant degree of selectivity can be achieved in the energy range of the created X-rays. A useful reduction in the intensity of created softer (undesired) bremsstrahlung is achieved already with the three-fold difference in Z illustrated in the example above, but the effect gets more significant as the difference in Z gets larger.

Figure 4:
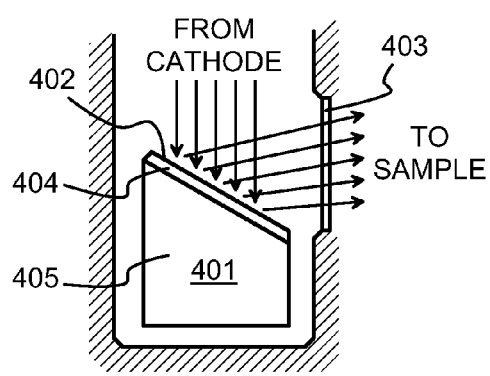
FIG. 4 illustrates parts of an X-ray tube according to an embodiment of the invention.

FIG. 4 illustrates parts of an X-ray tube according to an embodiment of the invention. The X-ray tube comprises a cathode, which acts as a source of electrons although it is not separately shown in FIG. 4. Additionally the X-ray tube comprises an anode 401 with an electron receiving surface 402. In the schematic representation of FIG. 4, the electron receiving surface is the surface of the anode that faces obliquely upwards. We assume that the cathode is located in the unshown top part of the X-ray tube, so that the field lines that represent the electron-accelerating electric field between the anode and the cathode are essentially vertical. The X-ray tube may comprise one or more electrostatic lenses that shape the electric field between the cathode and the anode, and consequently guide the accelerated electrons on their way towards the anode 401. The arrows pointing directly downwards represent the movement of the accelerated electrons.

The X-ray tube that is schematically illustrated in FIG. 4 if of the side window type. It comprises a window 403 facing the electron receiving surface 402 of the anode 401. The fact that the window 403 faces the electron receiving surface 402 should be interpreted so that at least some of the X-rays generated at the very surface of the anode 401 where the electrons hit have a direct propagation path to and out of the window 403, without having to pass through structural parts such as the rest of the anode. The arrows pointing right in FIG. 4 represent the propagation paths of the generated X-rays.

On the electron receiving surface 402 of the anode 401 there is a layer 404 of anode material. Even if the thickness of the layer 404 may be quite small compared to the mass and dimensions of the anode 401 as a whole, the expression "anode material" is used here to describe the layer 404; it is the bremsstrahlung that will be generated in this layer that should constitute the desired excitation radiation, for the production of which the X-ray tube will be used. Deeper in the anode 401 than the layer 404 of anode material—where "deeper" means further in the arrival direction of the electrons—the anode 401 comprises a block 405 of attenuator material. The atomic number of the attenuator material is less than one third of the atomic number of the anode material. In other words, the block 405 is made of a lighter material than the layer 404.

It is important to note that in this description the expression "attenuator material" does not refer to ability of said material to attenuate X-rays, but to its ability to gently (i.e. not as abruptly as heavier materials) slow down electrons so that only relatively little bremsstrahlung is generated. We may consider the roles of the two materials with reference to also FIG. 3.

Of the accelerated electrons that hit the electron-receiving surface 402 of the anode 401, some lose their whole kinetic energy in a single interaction with an atom or nucleus of the anode material (i.e. with an atom or nucleus that forms a part of the layer 404), like electron 302 in FIG. 3. Others continue through the layer 404 into the block 405 of attenuator material. If the layer 404 is extremely thin, there may be a significant number of electrons that do not interact at all in layer 404 and consequently still maintain their full kinetic energy when they enter the block 405. On the other hand, if the layer 404 is very thick, its stopping power may become so large that practically all electrons lose their kinetic energy already in the anode material, by undergoing even a number of interactions, before they could continue from the layer 404 of anode material into the block 405 of attenuator material. Somewhere between these extremes is an optimum thickness of the layer 404, so that a significant majority of the desired hard bremsstrahlung will be generated in it, but most of those electrons that do not lose a large majority of their kinetic energy in already one interaction leave the anode material and continue into the attenuator material below it.

In order to concretize the layer thicknesses, we may consider the task of analysing the gold content of a sample. Gold exhibits three published K-alpha lines, with energies ranging from approximately 68.8 keV to approximately 66.4 keV. The excitation energy used for the X-ray fluorescence analysis of gold must be higher than the absorption edge of gold, which is approximately 80.7 keV. There are no anode materials that would have useful characteristic lines that high, so as excitation energy one must use hard bremsstrahlung. If the acceleration voltage of the X-ray tube is 110 kV, electrons hitting the anode will have the initial energy 110 keV. If the anode material is tungsten, the electrons have lost an average 30 keV of their energy after penetrating 8 micrometers into the anode. In other words, deeper than 8 micrometers in the anode material, only electrons with energies less than 80 keV will be encountered. These cannot generate bremsstrahlung that would be hard enough to excite the K-alpha lines of gold, so they will only give rise to useless softer radiation that would only burden the detection system.

With the exemplary numerical values and materials mentioned above, we may thus deduce that a good selection for the thickness of the layer 404 would be 8 micrometers of tungsten. In order to stop 80 keV electrons, at least 55 micrometers of beryllium is needed. The beryllium block may naturally be made thicker, if this is needed for example to facilitate more effective cooling of the anode or to make the anode structurally stronger. Additionally or alternatively the anode may comprise other layers and structures made of other materials under the block of attenuator material, if these are advantageous for example to arrange effective cooling or to make the anode structurally strong enough.

Comparing to FIG. 3, we may suppose that the borderline between anode material and attenuator material is at depth 304. Since the atomic number of the attenuator material is less than one third of the atomic number of the anode material, it will give rise to less than one third of the softer bremsstrahlung that would be created if the whole anode would be made of the anode material.

As an example, we may consider that the anode material is molybdenum (with its atomic number Z=42) and the attenuator material is aluminium (Z=13). As another example, we may consider using erbium (Z=68) as the anode material, and aluminium (Z=13) as the attenuator material, in which case the atomic number of the attenuator material is less then one fifth of the anode material. Even more of the advantageous reduction of the softer bremsstrahlung can be achieved by selecting an even lighter material, such as carbon (Z=6) or beryllium (Z=4), as the attenuator material. With beryllium as the attenuator material, it is easy to reach a situation in which the atomic number of the attenuator material is less than one tenth of the atomic number of the anode material. This criterion is fulfilled already by using molybdenum as the anode material, but a very advantageous relation of atomic numbers is achieved by combining beryllium (Z=4) as the attenuator material with tungsten (Z=74) as the anode material, in which case the generated softer bremsstrahlung will be reduced by a factor 18.5 compared to the bremsstrahlung that a solid tungsten anode would cause. It is believed that significant advantages can be achieved with a solution according to the invention if the atomic number of the anode material is greater than or equal to 42 (which is the atomic number of molybdenum).

As a rule of thumb, we may suppose that the thickness of the layer of anode material in the propagation direction of electrons from the cathode to the anode is large enough to slow down electrons to the energy which equals the absorption edge of the element to be analysed in the sample. In typical applications the thickness of the layer of anode material is between 4 and 8 micrometers, and the thickness of the block of attenuator material is larger than 50 micrometers. If other structures are used in the anode behind the block of attenuator material, the thickness of the block of attenuator material is typically between 50 and 100 micrometers.

A combined thickness of the layer of anode material and the block of attenuator material in the propagation direction of electrons from the cathode to the anode should be larger than a maximum penetration depth in the combined stack of said layer of anode material and said block of attenuator material at a nominal acceleration voltage of the X-ray tube. In other words, with the sufficient thickness of the block of attenuator material it should be made sure that all electrons are stopped in the anode, in order to avoid potentially harmful beta radiation on the other side of the anode.

The fact that less bremsstrahlung is generated in the lighter attenuator material does not change the fundamental fact that the whole kinetic energy of all accelerated electrons must be either radiated away or absorbed in the anode eventually in the form of heat. Using an X-ray tube according to an embodiment of the invention in industrial scale, for example for analysing ore in a mine or an ore processing facility, typically calls for operating the X-ray tube at a relatively high power. This in turn means that anode cooling must be arranged for example by building water circulation in the anode. Also a rotating anode may be used in order to avoid continuously generating heat at only one, tightly focused spot in the anode. As such, anode cooling and anode rotating in X-ray tubes have been known for a very long time, so they need not be discussed further here. Any form of anode cooling and/or anode moving may be combined with the structural features typical of embodiments of the present invention.

Figure 5:
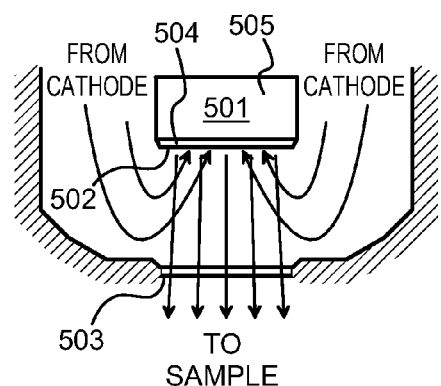
FIG. 5 illustrates parts of an X-ray tube according to another embodiment of the invention.

The invention is not limited to X-ray tubes of the side window type. FIG. 5 illustrates schematically an X-ray tube of the end window type, which comprises a cathode (not separately shown) for example in the form of a ring-shaped conductor located in a cylindrically symmetric fashion around a central axis of the X-ray tube. The X-ray tube comprises also an anode 501, with an electron receiving surface 502 which in FIG. 5 is downwards. At one end of the X-ray tube it comprises a window 503 facing the electron receiving surface 502 of the anode 501. Again, saying that the window faces the electron receiving surface means that at least some of the X-rays generated immediately on the electron receiving surface have a direct and unobstructed propagation path to and out of the window 503. The electric field lines between the cathode and the anode are curved, and consequently also the accelerated electrons follow curved paths, as illustrated by the curved arrows in FIG. 5.

On the electron receiving surface 502 of the anode 501 there is a layer 504 of anode material. Deeper in the anode 501 than said layer 502 of the anode material, considered in the arrival direction (upwards) of the electrons, the anode 501 comprises a block 505 of attenuator material. Just like in the embodiments described earlier with reference to FIG. 4, the atomic number of the attenuator material is less than one third of the atomic number of the anode material. The atomic number of the attenuator material may be less than one fifth, or less than one tenth, or even (like in the case of a tungsten layer on beryllium) less than one 18$^{th}$ of the atomic number of the anode material.

Figure 6:
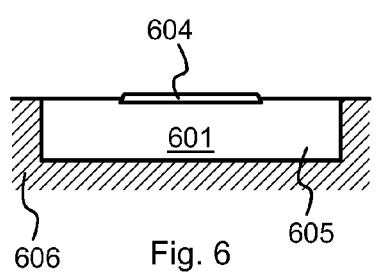
FIG. 6 illustrates an alternative anode structure.

The layer of anode material does not need to cover the whole electron-receiving surface of the anode; neither does the anode need to be constituted of only the layer of anode material and the block of attenuator material. As an example, FIG. 6 illustrates schematically an anode 601, the electron-receiving surface of which is its upper surface. A layer 604 of anode material only covers a part of the electron receiving surface. Deeper in the anode than the layer of anode material, and also at areas around the layer of anode material, the anode comprises a block 605 of attenuator material, with its atomic number less than one third of the atomic number of the anode material. In this case the block 605 of attenuator material resides in a cup-like holder 606 made of some other material. The holder could also be plate-like and located completely below the block 605 of attenuator material, or it could have any other shape found suitable for holding the anode. Having only a part of the electron-receiving surface covered with a layer of anode material may be a good solution for example in cases where a larger part of the anode surface actually receives accelerated electrons, but only from a smaller part of it there is a direct and unobstructed propagation path to and out of the window and further onto the optical path of the X-ray beam used for excitation. The principles illustrated schematically in FIG. 6 and/or explained above can easily be applied in all kinds of X-ray tubes according to embodiments of the invention.

An anode structure with three or more layers, like for example the one illustrated in FIG. 6, may be very advantageous because it allows selecting the materials for the different parts of the anode according to their specific properties and tasks in the anode. The actual anode material (layer 604 in FIG. 6) should be selected heavy enough so that it creates the desired hard bremsstrahlung. The attenuator material following it (block 605 in FIG. 6) should have as small atomic number as possible, in order to achieve the best possible reduction in the generation of unwanted, softer bremsstrahlung. However, such a very light material may have other disadvantageous characteristics like less than optimal thermal conductivity, high price, insufficient structural strength, or—like in the case of beryllium—toxicity. In order to stop the electrons that come through the layer of anode material, it may suffice to have a block of attenuator material only some tens of micrometers thick. The remaining layer(s) and structure(s) of the anode may be made of materials that have the sufficient structural strength, thermal conductivity, and other advantageous characteristics that are needed. An exemplary way of building an anode could be to use a copper or aluminium body in which cooling channels are formed; to solder, weld, or otherwise attach a 50-100 micrometers thick beryllium layer on a flat surface of said body; and to cover at least a part of the beryllium surface with a 4-8 micrometers thick tungsten foil.

Figure 7:
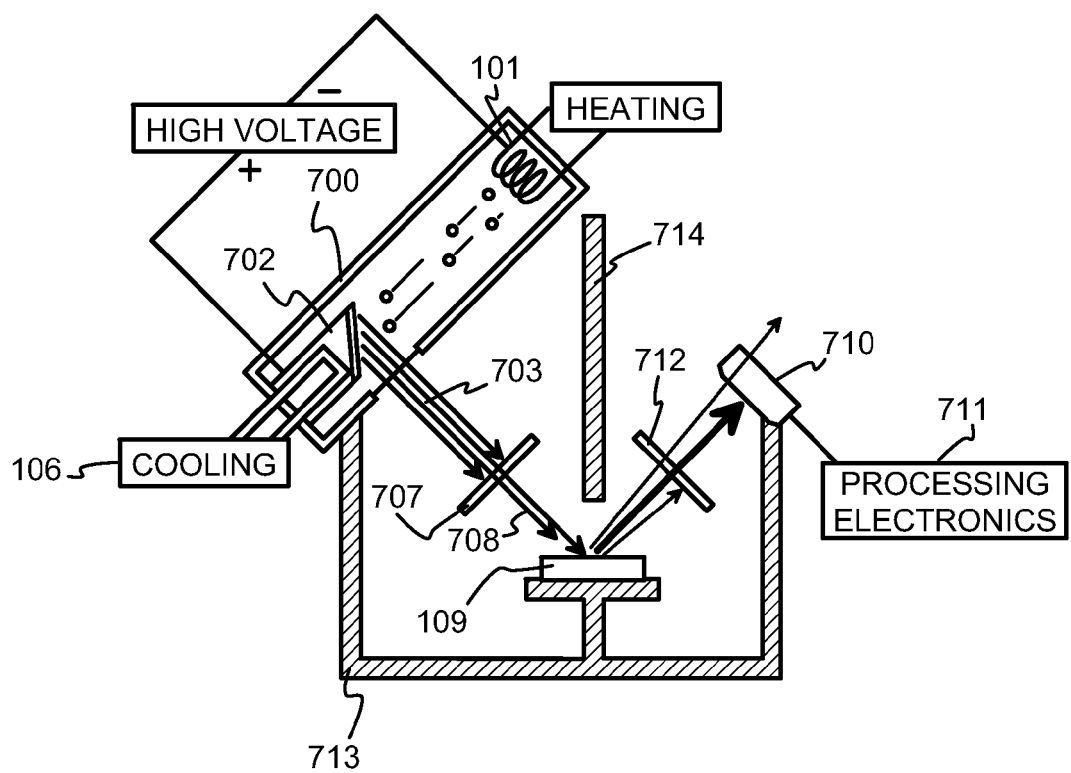
FIG. 7 illustrates an X-ray fluorescence analyser device according to an embodiment of the invention.

FIG. 7 illustrates schematically an X-ray fluorescence analyser device according to an embodiment of the invention. As the source of excitation X-rays, it comprises an X-ray tube 700 according to an embodiment of the invention, i.e. having an anode 702 in which a layer of anode material is followed by a block of attenuator material, with the atomic number of said attenuator material being less than one third of the atomic number of the anode material. Additionally the X-ray fluorescence analyser device illustrated in FIG. 7 comprises a detector 710 of fluorescent radiation. Various aspects of the device and certain advantageous, optional features are described in more detail in the following.

All in all it is advantageous that the X-ray fluorescence analyser device comprises a support frame for maintaining a known spatial relationship between the X-ray tube and a sample to be analysed, and between the sample and the detector. The known spatial relationship enables taking into account factors such as radiation divergence in various directions and spatial angle covered by the target and the detector, so that appropriate calculational corrections can be applied in processing the measurement results. In FIG. 7 the support frame is schematically illustrated with the reference designator 713. A separating wall 714 is also schematically illustrated, having the purpose of blocking any excitation radiation from propagating towards the detector 710.

In order to further reduce the probability of excitation X-rays hitting the detector, it is advantageous (although not mandatory) to arrange the positions, directions, and spatial relations of the X-ray tube, the sample, and the detector so that one can utilise the natural way in which the polarisation of X-rays depend on directional factors in an X-ray fluorescence analyser. The excitation beam propagation direction, i.e. the direction of the beam 703 out of the X-ray tube 700 and towards the sample 109 to be analysed, is at an essentially right angle to the propagation direction of accelerated electrons within the X-ray tube 700. The apparatus of FIG. 7 has an X-ray tube of the side window type, in which the propagation direction of accelerated electrons within the X-ray tube is the same as the central linear direction from the cathode 101 to the anode 702. The filtered excitation beam is separately shown in FIG. 7 with the reference designator 708, but its propagation direction is the same as that of the excitation beam 703 before filtering.

The fluorescence beam propagation direction from the sample 109 to the detector 710 of fluorescent radiation is at an essentially right angle to said excitation beam propagation direction. Fluorescent radiation emerges from the sample in all free directions, and in some cases the path of the fluorescent radiation may involve diffractive filters that change the propagation direction of the fluorescent radiation. It is advantageous to define the fluorescence beam propagation direction from the sample to the detector, mentioned above, as the initial direction of a ray that originates in the center of the sample area illuminated with the excitation beam, and that will, after passing through the path of the fluorescent radiation, hit the center point of the detector 710.

When the directions have been selected in the manner explained above, there will be a certain distribution of polarisations in the excitation beam, with an intensity maximum at a certain "most favourable" polarisation. Scattering of the excitation radiation from the sample takes place so that radiation at said most favourable polarisation has a scattered intensity minimum in the fluorescence beam propagation direction. Thus, simply by selecting the beam directions in the appropriate manner, the amount of scattered excitation radiation that hits the detector can be made smaller.

Although not mandatory, it is also advantageous to make the X-ray fluorescence analyser device comprise a primary filter 707 on the excitation beam propagation path between the X-ray tube 700 and the sample 109. The primary filter 707 is configured to essentially absorb characteristic X-ray peaks of the anode material of the X-ray tube. For example, if the anode material is tungsten, it is advantageous that the primary filter 707 comprises gadolinium. For other anode materials, correspondingly matching materials for the primary filter 707 can be found by comparing the X-ray attenuation characteristics of the possible filter materials to the characteristic peak energies of the anode materials. The use of polarisation effects have been thoroughly explained in the U.S. Pat. No. 6,049,589 of the same inventor. Said US patent is incorporated herein by reference.

In order to further reduce the amount of excitation radiation that would eventually end up hitting the detector, it is advantageous—but not mandatory—to make the X-ray fluorescence analyser device comprise a secondary X-ray filter 712 of low-pass type between the sample 109 to be analysed and the detector 710. Analogously with the case of the anode-material-specific primary filter, it is possible to optimise the material composition of the secondary filter 712 for particular material(s) of that are to be analysed in the sample, as well as for particular energies of the excitation radiation. For example, for analysing gold in the sample with excitation radiation from a tungsten anode, lead and/or bismuth could be selected as materials of the secondary filter 712. It is also possible to implement an X-ray filter of the low-pass type so that the filtering mechanism is not attenuation but diffraction, because the diffraction angles of X-rays depend on the energy of the X-rays.

As a yet another optional feature that can be used to reduce the loading effect of scattered excitation radiation on the processing electronics 711, a sufficiently thin germanium detector can be used as the detector 710 of the X-ray fluorescence analyser device. This way some of the energetic excitation radiation that despite all countermeasures reaches the detector will pass through the detector layer without giving rise to background noise in the significant energy ranges. Making the germanium detector sufficiently thin means that the detector has a detector layer made of germanium, and a dimension of the detector layer in the propagation direction of fluorescent X-rays from the sample to be analysed is less than the thickness of germanium needed to absorb some predetermined amount like 50% of X-rays at the energies of the excitation beam. This definition naturally depends on the acceleration voltage used in the X-ray tube, which determines the maximum energy of the excitation beam. Additionally the definition of a sufficiently thin detector layer depends on the thickness of the layer of anode material and the kind of primary and secondary filters (if any) that are in use, which all have an effect on both the amount and the energy spectrum of the excitation radiation that reaches the detector.

Exemplary embodiments that have been described above are not limiting. For example, even if the concept of a support frame has been introduced in singular and a single support frame is schematically represented in FIG. 7, it is naturally possible that the structures used to maintain a known spatial relationship between the X-ray tube and a sample to be analysed and between said sample to be analysed and the detector consist of several different mechanical entities. The known spatial relationships need not be fixed; indeed it is in many cases advantageous if there is a possibility to move the X-ray tube and/or the detector with respect to the sample, which increases the flexibility in arranging the measurement. Adjustable fittings may be used to implement movability, or the holding parts for at least one of the X-ray tube, the sample, and the detector may be equipped with actuators for automatic moving and control. Changes in the spatial relationships may be keyed in manually to the processing electronics, or there may be sensors that automatically detect the spatial relationships and consequently provide the processing electronics with appropriate information.

Another possible modification concerns the number of anodes, X-ray tubes, filters, and detectors that can be used in the X-ray fluorescence analyser device. For example the fluorescence induced by the excitation radiation of a single X-ray tube may be detected with two or more detectors, or an X-ray tube may have a rotating anode on the electron-receiving surface of which there are patches of two or more anode materials, so that the energy spectrum of the excitation beam varies as the anode rotates. More than one filter can be used both on the primary and the secondary side, and automatic rotation or other kind of changing can be applied to filters as well.

An advantage that can be achieved with the invention is better natural selectivity in the generation of excitation radiation. Since less filtering and other such measures are needed that inevitably cause attenuation of also the desired energies of excitation radiation, the same amount of useful excitation radiation can be produced with less energy used to operate the X-ray tube. Or, alternatively, with a given amount of energy to operate an X-ray tube, a larger amount of useful excitation radiation can be produced than in prior art analyser devices. The reduced amount of background radiation that reaches and gets registered in the detector also means that X-ray fluorescence analyses of samples can be made more accurate, and/or that less signal processing power is needed to operate the analyser than in prior art solutions.

I claim:

1. An X-ray tube, comprising:
   a cathode,
   an anode with an electron receiving surface, and
   a window facing the electron receiving surface of the anode;
   wherein the anode comprises:
   on the electron receiving surface of the anode, a layer of anode material, and
   deeper in the anode than said layer of anode material in the arrival direction of the electrons, a block of attenuator material, a lower surface of the layer of anode material being directly on top of an upper surface of the block of attenuator material, and
   wherein the atomic number of said attenuator material is less than one third of the atomic number of the anode material.

2. The X-ray tube according to claim 1, wherein the atomic number of said attenuator material is less than one fifth of the atomic number of the anode material.

3. The X-ray tube according to claim 1, wherein the atomic number of said attenuator material is less than one tenth of the atomic number of the anode material.

4. The X-ray tube according to claim 1, wherein said attenuator material is beryllium.

5. The X-ray tube according to claim 1, wherein:
   a thickness of said layer of anode material in the propagation direction of electrons from the cathode to the anode is between 4 and 8 micrometers, and
   a combined thickness of said layer of anode material and said block of attenuator material in the propagation direction of electrons from the cathode to the anode is larger than a maximum penetration depth of the electrons in the combined stack of said layer of anode material and said block of attenuator material at a nominal acceleration voltage of the X-ray tube.

6. The X-ray tube according to claim 1, wherein:
   a thickness of said block of attenuator material the propagation direction of electrons from the cathode to the anode is between 50 and 100 micrometers,
   said block of attenuator material resides in a holder made of a third material.

7. The X-ray tube according to claim 1, wherein the atomic number of said anode material is 42 or larger.

8. An X-ray fluorescence analyser device, comprising an X-ray tube according to claim 1 and a detector of fluorescent radiation.

9. The X-ray fluorescence analyser device according to claim 8, wherein:
   the X-ray fluorescence analyser device comprises a support frame for maintaining a known spatial relationship between the X-ray tube and a sample to be analyzed and between said sample to be analyzed and the detector,
   an excitation beam propagation direction out of the X-ray tube and towards said sample to be analyzed is at an essentially right angle to the propagation direction of accelerated electrons within the X-ray tube, and
   a fluorescence beam propagation direction from said sample to said detector of fluorescent radiation is at an essentially right angle to said excitation beam propagation direction.

10. The X-ray fluorescence analyser device according to claim 8, comprising a primary filter between the X-ray tube and the sample, wherein said primary filter is configured to essentially absorb characteristic X-ray peaks of the anode material of the X-ray tube.

11. The X-ray fluorescence analyser device according to claim 10, wherein the anode material of the X-ray tube is tungsten and the primary filter comprises gadolinium.

12. The X-ray fluorescence analyser device according to claim 8, comprising an X-ray filter, referred to as a secondary X-ray filter, of low-pass type between the sample to be analyzed and said detector.

13. The X-ray fluorescence analyser device according to claim 8, wherein said detector has a detector layer made of germanium, and a dimension of the detector layer in the propagation direction of fluorescent X-rays from the sample to be analyzed is less than the thickness of germanium needed to absorb 50% of X-rays at the energies of the excitation beam.

14. The X-ray fluorescence analyser device according to claim 9, comprising a primary filter between the X-ray tube and the sample, wherein said primary filter is configured to essentially absorb characteristic X-ray peaks of the anode material of the X-ray tube, and comprising an X-ray filter, referred to as a secondary X-ray filter, of low-pass type between the sample to be analyzed and said detector.

15. The X-ray fluorescence analyser device according to claim 10, comprising a secondary X-ray filter of low-pass type between the sample to be analyzed and said detector.

16. The X-ray fluorescence analyser device according to claim 9, wherein said detector has a detector layer made of germanium, and a dimension of the detector layer in the propagation direction of fluorescent X-rays from the sample to be analyzed is less than the thickness of germanium needed to absorb 50% of X-rays at the energies of the excitation beam.

17. The X-ray fluorescence analyser device according to claim 10, wherein said detector has a detector layer made of germanium, and a dimension of the detector layer in the propagation direction of fluorescent X-rays from the sample to be analyzed is less than the thickness of germanium needed to absorb 50% of X-rays at the energies of the excitation beam.

18. The X-ray fluorescence analyser device according to claim 11, wherein said detector has a detector layer made of germanium, and a dimension of the detector layer in the propagation direction of fluorescent X-rays from the sample to be analyzed is less than the thickness of germanium needed to absorb 50% of X-rays at the energies of the excitation beam.

19. The X-ray fluorescence analyser device according to claim 1, wherein a thickness of the layer of anode material is sufficiently thin such that a majority of hard bremsstrahlung generated by the anode will be generated in the layer of anode material and most of the electrons that do not lose a large majority of kinetic energy in one interaction leave the layer of anode material and continue into the block of attenuator material.

20. The X-ray fluorescence analyser device according to claim 1, wherein a thickness of the layer of anode material is between 4 and 8 micrometers and a thickness of the block of attenuator material is larger than 50 micrometers.

21. An X-ray tube having a structure decreasing an amount of soft bremsstrahlung that reaches a sample to be analysed, comprising:

- a cathode that provides a source of electrons with kinetic energy;
- an anode with an electron receiving surface that, in use, generates hard bremsstrahlung where the electrons hit the electron receiving surface, the electron receiving surface being a layer of anode material that generates hard bremsstrahlung, the anode comprising the layer of anode material directly on top of a block of attenuator material deeper in the anode than said layer of anode material in the arrival direction of the electrons, wherein the atomic number of said attenuator material is less than one third of the atomic number of the anode material; and
- a window facing the electron receiving surface of the anode so that at least some of the generated hard bremsstrahlung from the surface of the anode where the electrons hit have a direct propagation path to and out of the window to the sample to be analysed,
- wherein a thickness of the layer of anode material is sufficiently thin such that a majority of the hard bremsstrahlung will be generated in the layer of anode material and most of the electrons that do not lose a large majority of the kinetic energy in one interaction leave the layer of anode material and continue into the block of attenuator material.

* * * * *